(12) United States Patent
Smith et al.

(10) Patent No.: US 10,888,219 B2
(45) Date of Patent: *Jan. 12, 2021

(54) OPTICAL FIBER HAVING PROXIMAL TAPER FOR OPHTHALMIC SURGICAL ILLUMINATION

(71) Applicant: Alcon Inc., Fribourg (CH)

(72) Inventors: Ronald T. Smith, Irvine, CA (US); Alireza Mirsepassi, Irvine, CA (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/546,453

(22) Filed: Aug. 21, 2019

(65) Prior Publication Data
US 2019/0374098 A1    Dec. 12, 2019

Related U.S. Application Data

(63) Continuation of application No. 14/957,248, filed on Dec. 2, 2015, now Pat. No. 10,441,157.

(51) Int. Cl.
*A61B 3/00* (2006.01)
*A61F 9/007* (2006.01)
*F21V 8/00* (2006.01)

(52) U.S. Cl.
CPC ............ *A61B 3/0008* (2013.01); *A61F 9/007* (2013.01); *G02B 6/0006* (2013.01); *G02B 6/0008* (2013.01)

(58) Field of Classification Search
CPC ..... A61B 3/0008; A61F 9/007; G02B 6/0006; G02B 6/0008; G02B 6/0005; G02B 6/0001; G02B 6/0023; G02B 6/003; G02B 27/00; F21V 2200/00; F21V 2200/10; F21V 2200/13; F21V 2200/17
See application file for complete search history.

(56) References Cited

U.S. PATENT DOCUMENTS 6,272,269 B1 *   8/2001   Naum ................ G02B 6/0026
                                                          362/551

* cited by examiner

*Primary Examiner* — Bao Q Truong

(57) ABSTRACT

An ophthalmic illumination system can include an optical fiber configured to transmit a light beam output by a light source and focused by a condenser. The optical fiber can include proximal, distal, and central portions. The proximal portion can be configured to receive the light beam focused by the condenser. The distal portion can be configured to emit the light beam to illuminate a surgical field. The central portion can extend between the proximal and distal portions. A core diameter of the proximal portion can be larger than core diameters of the central and distal portions. An ophthalmic illumination method can include focusing, using a condenser, a light beam emitted by a light source onto a proximal portion of an optical fiber. The method can also include transmitting, using the optical fiber, the light beam to a surgical field.

20 Claims, 8 Drawing Sheets

| N | 1 | 2 | 3 | 4 | 5 | 6 |
|---|---|---|---|---|---|---|
| | | | $d_1$, MICRONS | | | |
| | 1 | 1 | 1 | 1 | 1 | 1 |
| 1 | 2.50 | 2.80 | 3.25 | 4.00 | 5.50 | 10.00 |
| 2 | 3.00 | 3.40 | 4.00 | 5.00 | 7.00 | 13.00 |
| 3 | 3.25 | 3.70 | 4.38 | 5.50 | 7.75 | 14.50 |
| 4 | 3.40 | 3.88 | 4.60 | 5.80 | 8.20 | 15.40 |
| 5 | 4.00 | 4.60 | 5.50 | 7.00 | 10.00 | 19.00 |
| INFINITY | | | | | | |

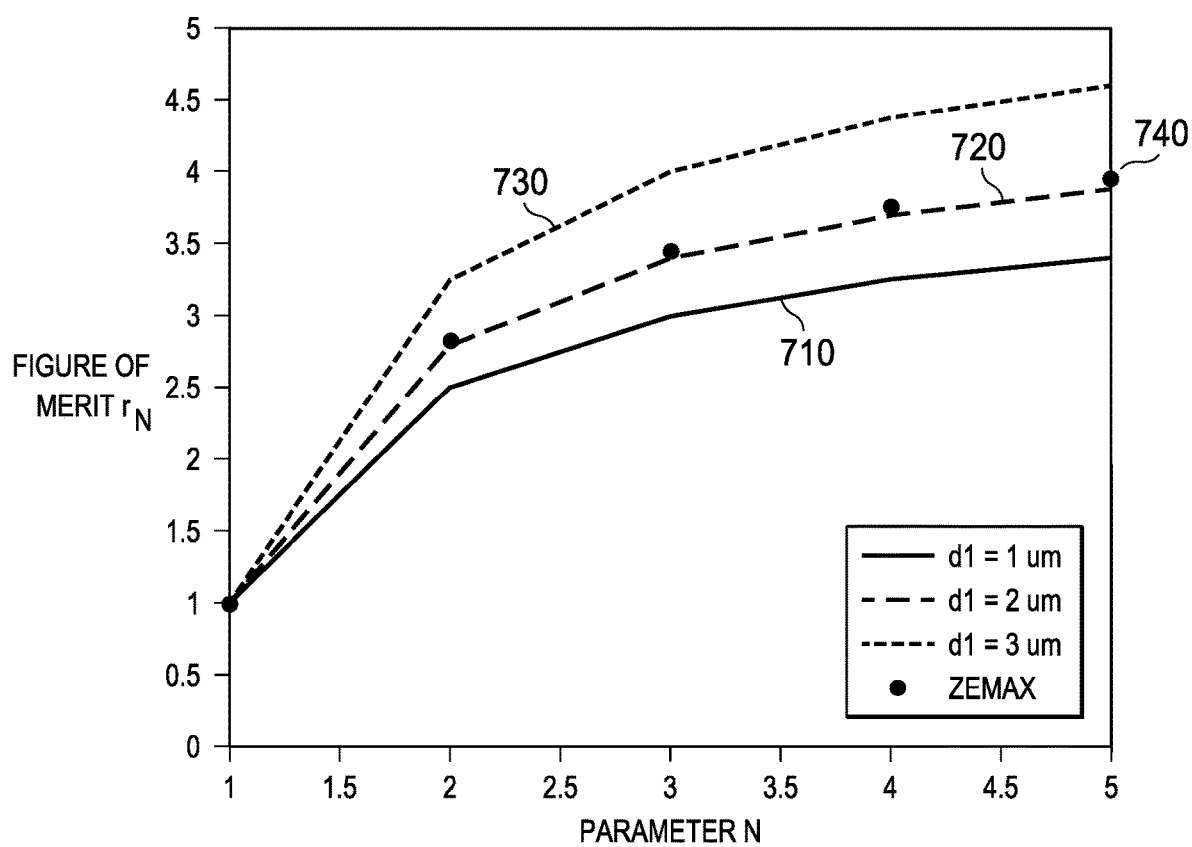

OPTICAL FIBER HAVING PROXIMAL TAPER FOR OPHTHALMIC SURGICAL ILLUMINATION

This application is a continuation application of U.S. patent application Ser. No. 14/957,248 titled "Optical Fiber Having Proximal Taper for Ophthalmic Surgical Illumination" which was filed Dec. 2, 2015 whose inventors are Ronald T. Smith and Alireza Mirsepassi which is hereby incorporated by reference in its entirety as though fully and completely set forth herein.

BACKGROUND

Technical Field

Embodiments disclosed herein can be related to ophthalmic illumination systems. More specifically, embodiments described herein can relate to illuminating a surgical field, such as a patient's eye, during ophthalmic procedures using an optical fiber having a tapered proximal portion. The tapered proximal portion can allow the optical fiber to efficiently receive a misaligned light beam.

Related Art

Ophthalmic microsurgical procedures can require precision cutting and/or removing of various body tissues of the patient's eye. During the procedures, ophthalmic illumination devices can provide light for the surgical field. A user, such as a surgeon or other medical professional, can insert the device into the eye to illuminate the inside of the eye. A light source and other illumination optics, such as a collimator and a condenser, direct a light beam towards an optical fiber of the illumination device.

During assembly of the illumination optics, manufacturers can try to optimize various parameters of the light beam associated with coupling the light beam into the optical fiber. For example, coupling efficiency can be a description of coupling the light beam into the optical fiber. High coupling efficiency can result in the transmission of relatively greater amounts of undistorted light from the light source to the surgical field, via the optical fiber. Low coupling efficiency can result in to less light being transmitted to the surgical field, as well as the light being transmitted with an undesired angular profile. One way of improving coupling efficiency during manufacture includes precisely aligning the illumination optics components (e.g., the collimator, the condenser, the optical fiber, etc.) and then immobilizing the components so that they do not subsequently become misaligned. For example, a beam spot of a condensed beam can be centered at the proximal end of the optical fiber upon alignment of the condenser and the optical fiber. However, any angular or lateral misalignment can cause a loss of optical coupling efficiency.

The coupling efficiency into the optical fiber can be sensitive to even small misalignments of the light beam into the condenser and/or other components. Misalignment can arise from different sources. Temperature changes during use can cause misalignment of a collimated beam into the condenser. For example, the climate surrounding the illumination optics can be atypically warm or cold, leading to thermal-induced expansion or compression of components. Vibration during use of the illumination optics can also cause misalignment. The illumination optics can be subject to mechanical shocks, such as being dropped during shipping or contacted by heavy equipment. These sources of error can be exacerbated by the inclusion of other optical components, such as fold mirrors and beam splitters. Temperature changes, vibration, and/or shock can cause the illumination optics and the light beam reflecting off of them to become misaligned. Furthermore, over the life of the illumination optics, slow creep of adhesive-based or mechanical-based mounts can cause the illumination optics and the light beam reflecting off them to become misaligned.

In some illumination optics assemblies, even angular misalignment by as little as approximately 0.01° can cause a significant decrease in the amount of light transmitted through the optical fiber. Because of the relatively high sensitivity to misalignment, maintaining high fiber coupling efficiency at all temperatures and operating conditions for the life of the illumination optics assembly can be important. An assembly that includes means of sensing and actively correcting for losses in fiber coupling efficiency by moving the condenser and/or other optical components may address some concerns. However, because of its high complexity and cost, such a coupling-efficiency sensor and active-feedback optical-alignment system would be difficult to design and implement in a cost-effective manner.

Accordingly, there remains a need for improved devices, systems, and methods that accommodate misalignment of a light beam while maintaining high coupling efficiency by addressing one or more of the needs discussed above.

SUMMARY

The presented solution fills an unmet medical need with a unique solution to reduce the sensitivity of an ophthalmic illumination system to misalignment of a light beam. The ophthalmic illumination system can include an optical fiber having tapered proximal portion. The tapered proximal portion can have a larger core diameter than more distal portions of the optical fiber. The tapered proximal portion can act as a funnel by more efficiently coupling even misaligned light into the optical fiber. As a result, the ophthalmic illumination system can be less sensitive to misalignment. The ophthalmic illumination system can also include a condenser configured to direct a condensed beam towards the optical fiber based on the larger core diameter of the tapered proximal portion.

Consistent with some embodiments, an ophthalmic illumination apparatus can be provided. The apparatus can include an optical fiber configured to transmit a light beam output by a light source and focused by a condenser. The optical fiber can include a proximal portion configured to receive the light beam focused by the condenser, a distal portion configured to emit the light beam to illuminate a surgical field, and a central portion extending between the proximal portion and the distal portion. A core diameter of the proximal portion can be larger than a core diameter of the central portion and a core diameter of the distal portion.

Consistent with some embodiments, an ophthalmic illumination method can be provided. The method can include focusing, using a condenser, a light beam emitted by a light source onto a proximal portion of an optical fiber. The optical fiber can include the proximal portion, a distal portion, and a central portion extending between the proximal portion and the distal portion. A core diameter of the proximal portion can be larger than a core diameter of the central portion and a core diameter of the distal portion. The method can also include transmitting, using the optical fiber, the light beam to a surgical field.

Additional aspects, features, and advantages of the present disclosure will become apparent from the following detailed description.

BRIEF DESCRIPTION OF THE DRAWINGS

FIG. 7 is a graph illustrating the figure of merit of FIG. 6.

Figure 1:
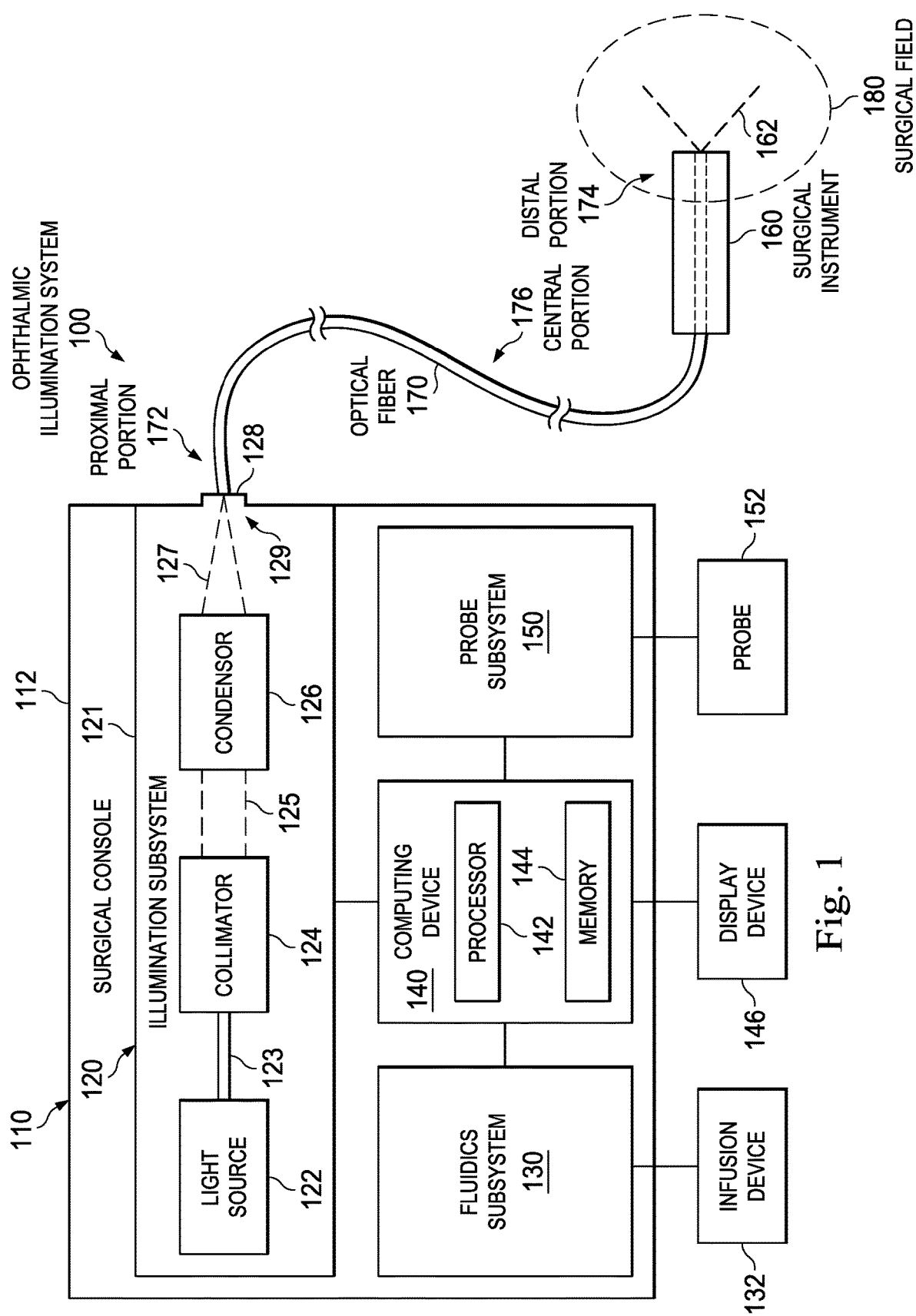
FIG. 1 is a diagram illustrating an ophthalmic illumination system.

In the drawings, elements having the same designation have the same or similar functions.

DETAILED DESCRIPTION

In the following description, specific details can be set forth describing certain embodiments. It will be apparent, however, to one skilled in the art that the disclosed embodiments may be practiced without some or all of these specific details. Specific and/or illustrative, but not limiting, embodiments can be presented herein. One skilled in the art will realize that other material, although not specifically described herein, can be within the scope and spirit of this disclosure.

The present disclosure describes devices, systems, and methods of optically coupling a light beam into an optical fiber in a manner that tolerates unintended angular or lateral misalignment of the light beam. A light source can generate a light beam for illuminating a surgical field, such as a patient's eye. A condenser can focus and direct the light beam towards the optical fiber. The condensed beam may be misaligned in some instances. The optical fiber includes a tapered proximal portion configured to receive the condensed beam while maintaining relatively high coupling efficiency. The proximal portion of the optical fiber has a core diameter that can be larger than the core diameters of the central and distal portions. The condenser can be configured to direct the condensed beam to the optical fiber based on the relatively larger core diameter of the tapered proximal portion.

The devices, systems, and methods of the present disclosure provide numerous advantages, including:

(1) The ophthalmic illumination system of the present disclosure can better tolerate alignment errors between a light beam and a light source, a collimator, a condenser, and/or other components of the ophthalmic illumination system. An optical fiber with only a straight proximal portion can be unable to accept misaligned light. In this context, the optical fiber with the enlarged diameter proximal portion can efficiently transmit even misaligned light.

(2) High coupling efficiency can be maintained despite alignment errors. The enlarged diameter proximal portion of the optical fiber can advantageously couple light that would have otherwise been lost due to alignment errors.

(3) Temperature-related, vibration-related, and/or shock-related errors can be accounted for. Misalignment can result from any one or more of these errors. By efficiently coupling even misaligned light, the optical fiber including the enlarged diameter proximal portion can account for multiple sources of error.

(4) The robustness of the ophthalmic illumination system to temperature variations, vibration, and/or shock can be improved. Even if the ophthalmic illumination system experiences these sources of alignment error, the ophthalmic illumination system can efficiently couple light into the optical fiber because the enlarged diameter proximal portion accounts for the misalignment.

(5) The lifespan of the ophthalmic illumination system can be increased. Optical misalignment can result over the life of the ophthalmic illumination system, including as the result of adhesive or mechanical degradation, as well as vibration during ordinary operation. Because the optical fiber accepts relatively greater amounts of misaligned light, the ophthalmic illumination system can be utilized even when the misalignment errors arise.

An ophthalmic illumination system 100 can be illustrated in FIG. 1. The ophthalmic illumination system 100 can include a light source 122. The light source 122 can be configured to output a light beam to illuminate a surgical field 180. The ophthalmic illumination system 100 can also include a condenser 126 having a plurality of lenses. The condenser 126 can be configured to focus the light beam outputted by the light source 122. The ophthalmic illumination system 100 can also include an optical fiber 170 configured to transmit the light beam focused by the condenser 126. The optical fiber 170 can include a proximal portion 172 configured to receive the light beam focused by the condenser 126, a distal portion 174 configured to emit the light beam within the surgical field 180, and a central portion 176 extending between the proximal portion 172 and the distal portion 174. A core diameter of the proximal portion 172 can be larger than a core diameter of the central portion 176 and a core diameter of the distal portion 174. The ophthalmic illumination system 100 can also include the surgical instrument 160 configured to be positioned within surgical field 180. The optical fiber 170 can be coupled to the surgical instrument 160.

The ophthalmic illumination system 100 can be used during various ophthalmic surgical procedures within the surgical field 180, such as the patient's eye. Exemplary ophthalmic surgical procedures can include a diagnostic procedure, a therapeutic procedure, an anterior segment procedure, a posterior segment procedure, a vitreoretinal procedure, a vitrectomy procedure, a cataract procedure, and/or other suitable procedures. The surgical field 180 can include any suitable physiology of the patient's eye, including an anterior segment, a posterior segment, a cornea, a lens, a vitreous chamber, a retina, and/or a macula.

The surgeon can view the surgical field 180 when illuminated by light from the light source 122. The light source 122 can be any suitable light source operable to output a light beam optically coupled into the optical fiber 170, as discussed herein. For example, the light source can include a laser source, such as a supercontinuum laser source, an incandescent light bulb, a halogen light bulb, a metal halide light bulb, a xenon light bulb, a mercury vapor light bulb, a light emitting diode (LED), other suitable sources, and/or combinations thereof. The light source 122 can output a diagnostic light beam, a treatment light beam, and/or an illumination light beam. The light beam can include any suitable wavelength(s) of light, such as a visible light, infrared light, ultraviolet (UV) light, etc. For example, the light beam can transmit bright, broadband, and/or white light to illuminate the surgical field 180.

The light beam can traverse an optical path extending between the light source 122 and the surgical field 180, including through a collimator 124, the condenser 126, and the optical fiber 170. The collimator 124 can be positioned in an optical path between the light source 122 and the surgical field 180 to receive the light beam output by the light source 122. The collimator 124 can include one or more lenses and/or other suitable optical components configured to align the light beam output by the light source 122. An optical fiber 123 that facilitates transmission of the light beam can be mechanically and/or optically coupled with and extend between the light source 122 and the collimator 124. The collimator 124 can collimate the light beam output by the light source 122 to generate a collimated beam 125. The collimated beam 125 can be a diverging, parallel, or converging beam.

The condenser 126 can be positioned in the optical path between the light source 122 and the surgical field 180, or between the collimator 124 and the surgical field 180, to receive the collimated beam 125. The collimated beam 125 can be transmitted through air or free space from the collimator 124 to the condenser 126. The condenser 126 can be configured to bend and/or otherwise interact with the collimated light beam 125 to generate the condensed beam 127. The condensed beam 127 can have a smaller spatial cross-section and/or beam diameter than the collimated beam 125. In that regard, the condensed beam 127 can be a converging beam. For example, the condenser 126 can be configured to focus the condensed beam 127 to a beam spot 129. The condenser 126 can include one, two, three, four, five, or more lenses and/or other suitable optical components. Exemplary lenses can include a biconcave lens, a biconvex lens, a convex-concave lens, a plano concave lens, a plano convex lens, a positive/negative meniscus lens, an aspheric lens, a converging lens, a diverging lens, and/or combinations thereof. The condenser 126 can have any suitable lens arrangement, including one or more singlets and one or more doublets.

Figure 2A:
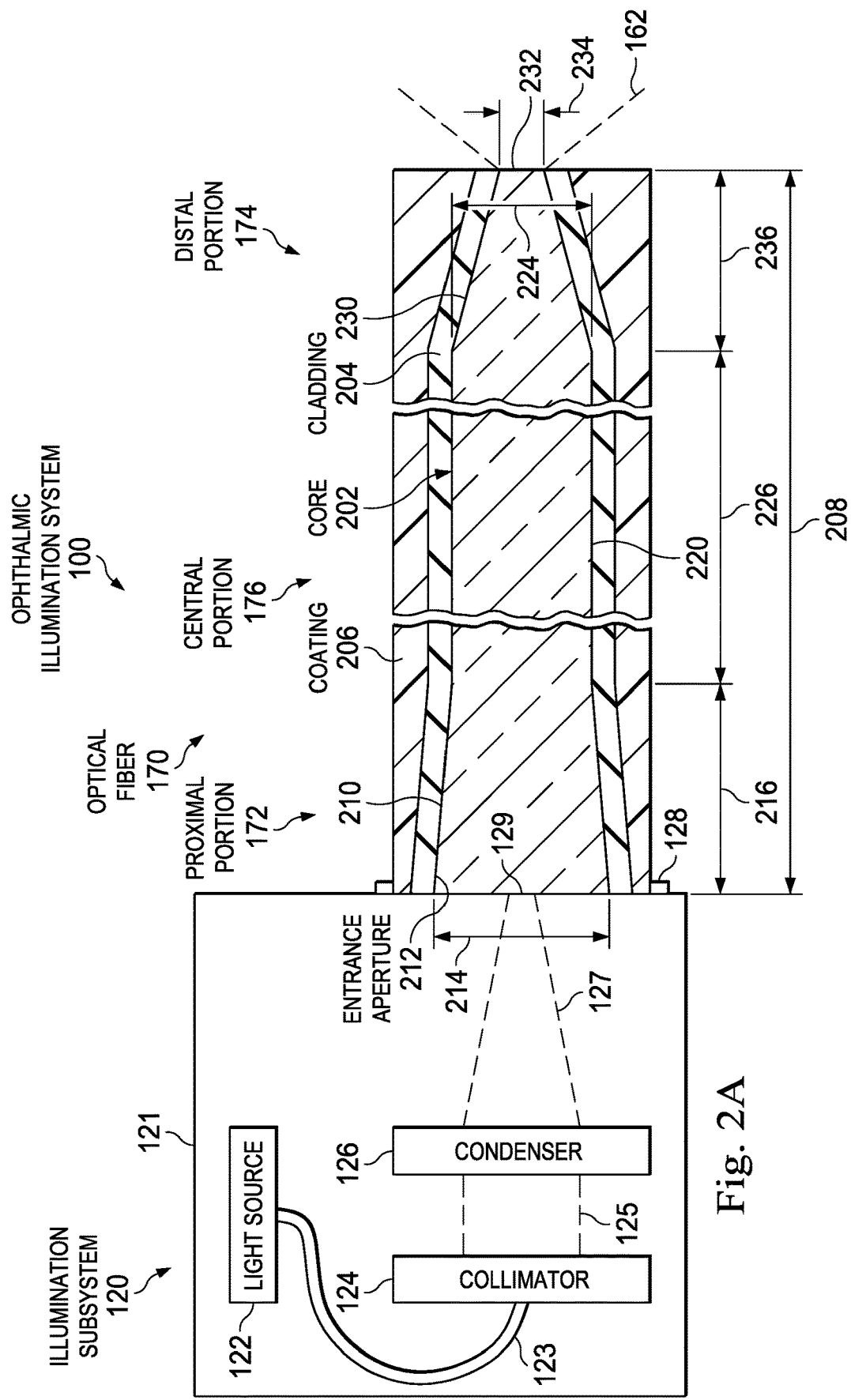
FIG. 2A is a diagram illustrating a portion of an ophthalmic illumination system, including an illumination subsystem and an optical fiber.
Figure 2B:
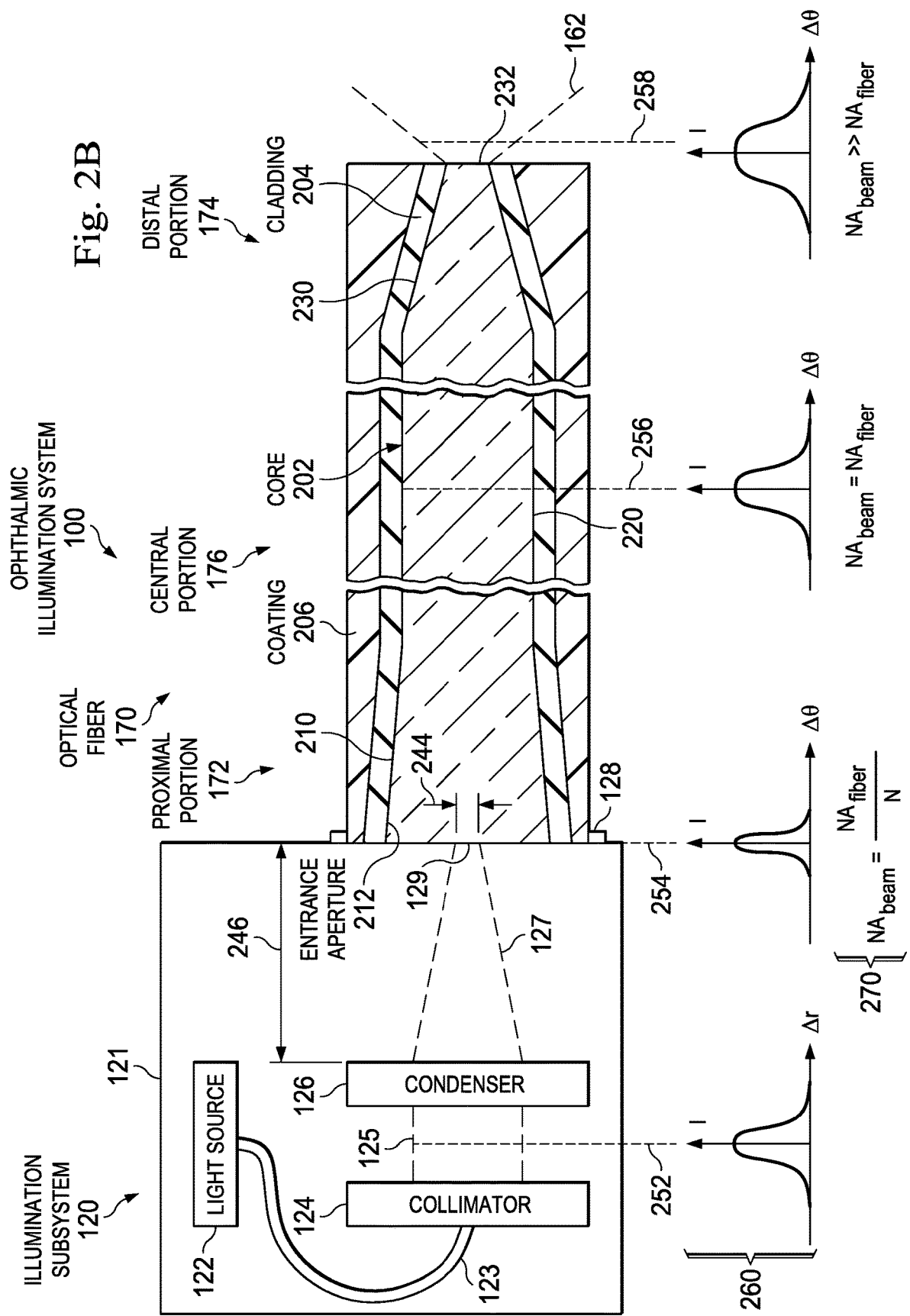
FIG. 2B is a diagram illustrating a portion of an ophthalmic illumination system, including an illumination subsystem and an optical fiber.
Figure 2C:
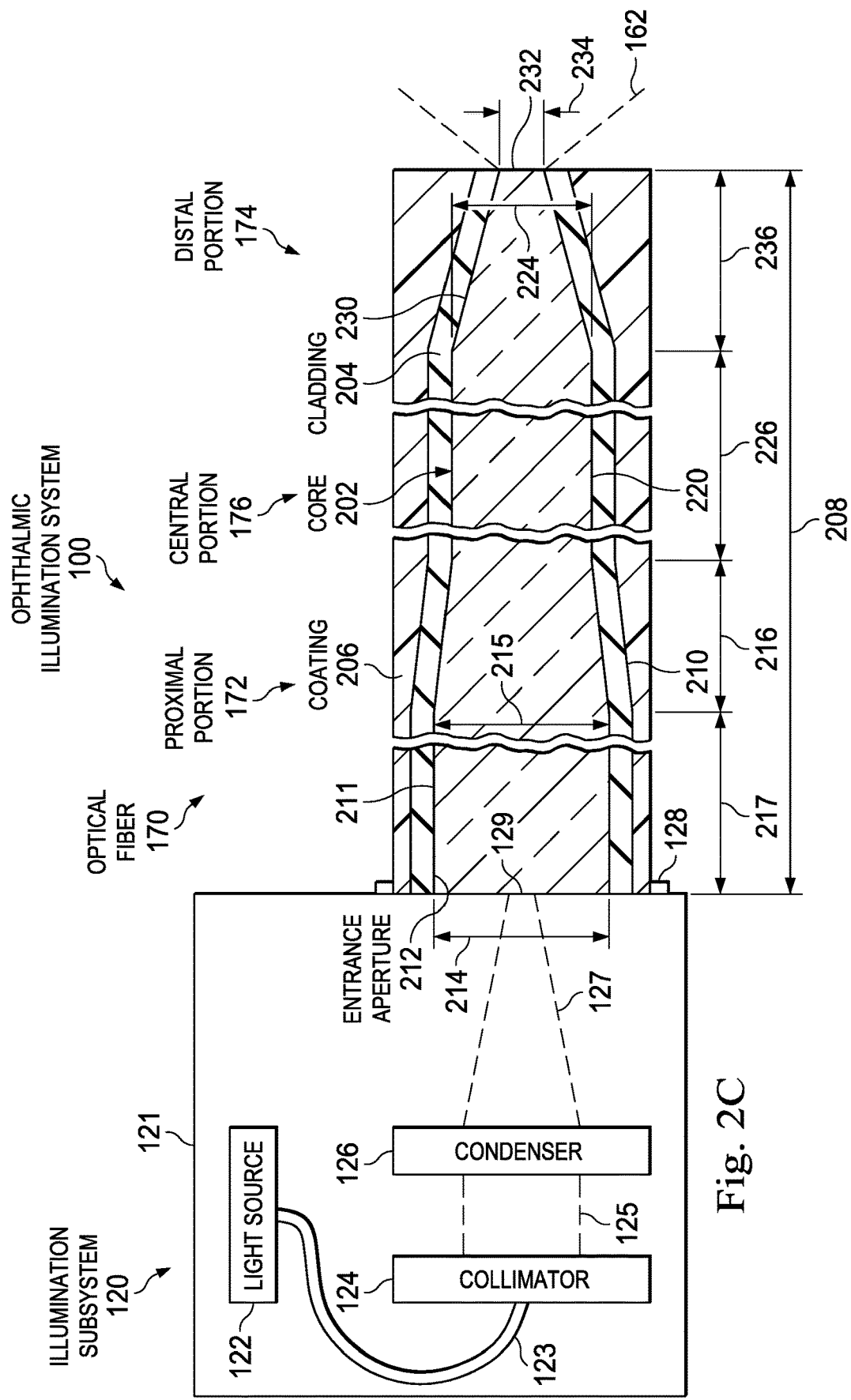
FIG. 2C is a diagram illustrating a portion of an ophthalmic illumination system, including an illumination subsystem and an optical fiber.

From the condenser 126, the condensed beam 127 can be transmitted to the optical fiber 170 through air/free space or another optical fiber. FIGS. 2A, 2B, and 2C can illustrate additional details of the optical fiber 170. The optical fiber 170 can be configured to transmit light from the light source 122 to the surgical field 180. In general, as illustrated in FIG. 1, the optical fiber 170 can include the proximal portion 172, the distal portion 174, and the central portion 176. The proximal portion 172 can receive the condensed beam 127 from the condenser 126. Once received at the proximal portion 172, the light propagates distally along the optical fiber 170 towards the surgical field 180. The central portion 176 can extend and transmit light between the proximal portion 172 and the distal portion 174. The distal portion 174 can deliver emitted light 162 into the surgical field 180. At least a portion of the optical fiber 170, such as the distal portion 174, can be positioned within the surgical field 180.

In that regard, the optical fiber 170 can be a disposable component configured for single use. For example, the distal portion 174 can be coupled to the surgical instrument 160 positioned within the surgical field 180. The distal portion 174 can be disposed within or coupled to an exterior of the surgical instrument 160. The central portion 176 and/or the proximal portion 172 can also be coupled to the surgical instrument 160. The surgical instrument 160 can be any suitable tool used by the surgeon during the ophthalmic surgical procedure, including a spot illuminator, a chandelier illuminator, an endoilluminator, an infusion cannula, a cutting probe, a vitrectomy probe, an aspiration probe, scissors, and forceps, for example. The surgical instrument 160 can be an infusion device 132 or a probe 152, described in greater detail below.

The light source 122, the collimator 124, and the condenser 126 can be part of an illumination subsystem 120. The optical fiber 170 can be in optical communication with the illumination subsystem 120. The illumination subsystem 120 can include all or a portion of the optical components associated with delivering light to the surgical field 180. The illumination subsystem 120 can include various other optical components, such as mirrors, including hot or cold dichroic mirrors and fold mirrors, beam splitters, lenses, gratings, filters, and/or combinations thereof, which facilitate transmission of light to the surgical field 180. The light source 122, the collimator 124, and the condenser 126 can be disposed within a housing 121 of the illumination subsystem 120. The housing 121 can be any suitable enclosure that maintains the light source 122, the collimator 124, and the condenser 126 in a fixed arrangement relative to one another. For example, light can be efficiently transmitted upon alignment of the light source 122, the collimator 124, the condenser 126, and/or the optical fiber 170. The housing 121 can include a base plate. The light source 122, the collimator 124, and the condenser 126 can be mounted, affixed, and/or otherwise mechanically coupled to the base plate so as to prevent unintended movement of the components. As discussed herein, such movement can adversely impact optical coupling efficiency. FIGS. 1, 2A, and 2B illustrate an unfolded optical path between the light source 122 and the surgical field 180. The optical path can include fold mirrors, beam splitters, and/or other optical components to guide the light beam within the physical structure of the housing 121. Fold mirrors can allow the illumination optics to fit into a compact volume. Beam splitters can facilitate the delivery of light to multiple fiber ports.

Referring again to FIG. 1, the optical fiber 170 can be mechanically coupled to the housing 121 of the illumination subsystem 120 at a port 128. The port 128 can be a component of the housing 121. The port 128 can be rigidly positioned relative to the light source 122, the collimator 124, the condenser 126, and/or other components of the illumination subsystem 120. For example, the port 128 may include mechanical features, such as threads, projections, grooves, to facilitate removable, mechanical coupling between the proximal portion 172 of the optical fiber 170 and the housing 121. The beam spot 129 of the condensed beam 127 can be centered within the port 128. The proximal portion 172 of the optical fiber 170 can be coupled to the housing 121 at the port 128. Proper alignment of the light source 122, the collimator 124, the condenser 126, and/or the optical fiber 170 can ensure proper centering of the beam spot 129 within the port 128 and efficient coupling of the condensed beam 127 into the optical fiber 170. As described herein, the ophthalmic surgical system 100 can be less susceptible to degradation in optical coupling efficiency as a result of misalignment of the light source 122, the collimator 124, the condenser 126, and/or the optical fiber 170.

The illumination subsystem 120 can be a standalone component or integrated in a surgical console 110. The surgeon can utilize the surgical console 110 to control one or more parameters associated with the ophthalmic surgical procedure. The surgical console 110 can include the illumination subsystem 120, a fluidics subsystem 130, a computing device 140, and a probe subsystem 150. One or more components of the surgical console 110 can be coupled to and/or disposed within a base housing 112. The base housing 112 can be mobile such that it can be positioned proximate to the patient during the ophthalmic surgical procedure. The base housing 112 can include pneumatic, optical, fluid, and/or electrical supply lines facilitating communication between components of the ophthalmic illumination system 100.

The computing device 140 can be configured transmit control signals to and/or receive input or status signals from one or components of the ophthalmic illumination system 100, such as the infusion device 132, the probe 152, and/or the surgical instrument 160. For example, the computing device 140 can control activation and deactivation of the light source 122, as well as the intensity, wavelength, and/or other characteristics of light output by the light source 122. In that regard, the light source 122 and/or the illumination subsystem 120 can be in electrical communication with the computing device 140. The computing device 140 can include a processing circuit having a processor 142 and a memory 144. The processor 142 can execute computer instructions, such as those stored on the memory 144, to control various subsystems and their associated surgical tools. The processor 142 can be a targeted device controller and/or a microprocessor. The memory 144, such as semiconductor memory, RAM, FRAM, or flash memory, can interface with the processor 142. As such, the processor 142 can write to and read from the memory 144, and perform other common functions associated with managing memory 144. The processing circuit of the computing device 140 can be an integrated circuit with power, input, and output pins capable of performing logic functions. The computing device 140 can be in communication with a display device 146 showing data relating to system operation and performance during an ophthalmic surgical procedure.

The fluidics subsystem 130 can be in electrical communication with the computing device 140. The fluidics subsystem 130 can include various components facilitating operation of an infusion device 132, such as the start/stop, rate, pressure, volume of fluid. The infusion device 132 may deliver fluid into the patient's eye to maintain intraocular pressure during the ophthalmic surgical procedure. The infusion device 132 may be in fluid and/or electrical communication with the fluidics subsystem 130.

The probe subsystem 150 can be in electrical communication with the computing device 140. The probe subsystem 150 can include various components facilitating operation of the probe 152. The surgeon can utilize the probe 152 within the surgical field 180 to perform one or more surgical maneuvers. For example, the probe 152 can be a cutting probe, a vitrectomy probe, a phacoemulsification probe, a laser probe, an ablation probe, a vacuum probe, a flushing probe, scissors, forceps, an aspiration device, and/or other suitable surgical device. The probe 152 may be in mechanical, electrical, pneumatic, fluid, and/or other suitable communication with the probe subsystem 150.

Portions of the ophthalmic illumination system 100, including the illumination subsystem 120 and the optical fiber 170, can be illustrated in FIGS. 2A, 2B, and 2C. FIGS. 2A, 2B, and 2C can illustrate a cross-sectional view of the optical fiber 170. The optical fiber 170 can include a core 202, cladding 204, and a coating 206. The core 202 can be cylinder of glass, plastic, silica, borosilicate, and/or other suitable material through which light propagates. The cladding 204 can surround the core 202 and confine the light within the core 202. The cladding 204 can include a dielectric material with an index of refraction less than the index of refraction of the core 202. The coating 206 can surround the cladding 204 and protect the optical fiber 170 from physical damage.

The condenser 126 can direct the focused beam 127 onto the proximal portion 172 of the optical fiber 170. The core 202 within the proximal portion 172 of the optical fiber 170 can include a tapered section 210. For example, the condenser 126 can direct the focused beam 127 onto the tapered section 210, as illustrated in FIGS. 2A and 2B. In that regard, the diameter and the cross-sectional area of the core 202 within the tapered section 210 can decrease distally along the optical fiber 170. The core 202 can include an entrance aperture 212 located at the proximal-most end of the optical fiber 170. The entrance aperture 212 can be a part of the core 220. For example, the entrance aperture 212 can be a proximal face of the core 202 that interfaces with the condensed beam 127. The entrance aperture 212 can be a part of the tapered section 210. The entrance aperture 212 can have a diameter 214, illustrated in FIGS. 2A and 2C. The diameter 214 of the entrance aperture 212 and/or the diameter 215 of a section 211 can be the largest diameter of the core 202 along a length 208 of the optical fiber 170. The condensed beam 127 can be optically coupled into the optical fiber 170 at the entrance aperture 212. For example, the beam spot 129 can ideally be centered within the entrance aperture 212. The tapered section 210 can be similar to a funnel with an enlarged diameter to receive the condensed beam 127. Advantageously, the tapered section 210 can be sized and shaped to allow high coupling efficiency by accommodating misalignment of the beam spot 129 and/or condensed beam 127.

As illustrated in FIG. 2C, the core 202 within the proximal portion 172 of the optical fiber 170 can include a section 211 having a constant size and shape. For example, the section 211 can be a straight, non-tapered section. The condenser 126 can direct the focused beam 127 onto the section 211. The section 211 can be positioned proximally of the tapered section 210. The entrance aperture 212 can be a part of the section 211. The section 211 can have a diameter 215 and a length 217. The diameter 215 of the section 211 can be substantially equal to the diameter 214 of the entrance aperture 212. The diameter 215 and the cross-sectional area of the section 211 can remain constant along the length 217 of the optical fiber 170. The length 217 can be related to the diameter 215 by a mathematical relationship. For example, the ratio of the length 217 and the diameter 215 can be greater than one thousand. When the length 217 and the diameter 215 satisfy this relationship, the light within the optical fiber 170 can laterally spread out as the light laterally fills the core 202. Thus, the light can become spatially homogenized within the section 211, before the light encounters the tapered region 210. This can be true even with misalignment of the beam spot 129 and/or components of the illumination subsystem 120 because the length 217 is sufficiently large to allow the light to laterally spread out and become spatially homogenized within the section 211. Thus, advantageously, the transmittance of light through tapered section 210 can be unaffected by the misalignment of the beam spot 129 and/or components of the illumination subsystem 120 because the light passed through the section 211 before encountering the tapered section 210.

The core 202 within the central portion 176 of the optical fiber 170 can include a section 220 having a constant size and shape. For example, the section 220 can be a straight, non-tapered section. The section 220 can have a diameter 224. The diameter 224 and the cross-sectional area of the section 220 can remain constant along the central portion 176 of the optical fiber 170.

The core 202 within the distal portion 174 of the optical fiber 170 can include a tapered section 230. In that regard, the diameter and the cross-sectional area of the core 202 within the tapered section 230 can decrease distally along the optical fiber 170. The tapered section 230 can terminate at a tip 232 at the distal-most end of the optical fiber 170. Emitted light 162 can be delivered into the surgical field 180 via the tip 232. The tip 232 can have a diameter 234. The tapered section 230 can include a borosilicate taper, for example. The tapered section 230 can be configured to output the emitted light 162 with a relatively large or a relatively small angular spread to illuminate the surgical field 180. The cladding 204 in the tapered section 230 can be stripped from the optical fiber 170 in some examples. The core 202 within the distal portion 174 of the optical fiber 170 can have a constant size and shape in some examples. For example, core 202 within the distal portion 174 can be a straight, non-tapered section. The core 202 within the distal portion 174 can have a diameter that increases distally along the optical fiber 170, in some examples. For example, the core 202 can be a tapered section with an increasing diameter. The core 202 within the distal portion 174 of the optical fiber 170 can include a scattering section in lieu of or in addition to the tapered section 230 in some examples. The tip 232 can be variously sized and shaped, including conically-shaped, spherically-shaped, and/or otherwise suitably shaped, to facilitate output of the emitted light 162 within the surgical field 180 with the desired angular spread.

The diameter of the core 202 can vary between the proximal portion 172, the central portion 176, and the distal portion 174 of the optical fiber 170. The diameter 224 within the section 220 can be generally described as $d_{fiber}$. For example, the value of $d_{fiber}$ can be between approximately 10 μm and approximately 100 μm, between approximately 10 μm and approximately 50 μm, between approximately 20 μm and approximately 30 μm, including values such as 20 μm, 22 μm, 25 μm, 27 μm, 30 μm, and/or other suitable values, both larger and smaller. The diameter 214 of the entrance aperture 212 can be a multiple of the diameter 224 and generally described as $N \cdot d_{fiber}$. The parameter N can thus describe the larger size of the entrance aperture 212 relative to the diameter 224 of the central portion 176. The value of the parameter N can be between 1 and 10, between 1 and 5, between 2 and 4, including, values such as 2, 2.5, 3, 3.1, 3.3, 4, and/or other suitable values, both larger and smaller. The value of the parameter N can be selected to achieve improved transmission of misaligned light while advantageously preserving a relatively small diameter (e.g., the diameter 214) for the optical fiber 170. The relatively small diameter of the optical fiber 170 can allow the optical fiber 170 to be advantageously integrated in various surgical instruments (e.g., the surgical instrument 160). The diameter 215 of the section 211 (FIG. 2C) can be substantially equal to the diameter 214 of the entrance aperture 212. The diameter of the tapered section 210 within the proximal portion 172 can decrease distally from $N \cdot d_{fiber}$ at the entrance aperture 212 or the section 211, to $d_{fiber}$ at the central portion 176. The diameter 234 of the tip 232 can be any suitable size equal to or smaller than $d_{fiber}$ of the diameter 224. The diameter 234 of the tip 232 can also be larger than $d_{fiber}$ of the diameter 224 in some examples. The value of diameter 234 of the tip 232 can be between approximately 1 μm and approximately $d_{fiber}$ of the diameter 224, and/or other suitable values, both larger and smaller. The diameter of the tapered section 230 within the distal portion 174 can decrease distally from $d_{fiber}$ at the central portion 176 to the diameter 234 at the tip 232. Thus, the diameter of the core 202 within the proximal portion 172 can be larger than the diameter of the core 202 in the central portion 176 and the distal portion 174. The diameter of the core 202 within the central portion 176 can be larger than the diameter of the core 202 in the distal portion 174.

The optical fiber 170 can have any suitable length 208. For example, the length 208 can be between approximately 0.1 m and approximately 3 m, between approximately 1 m and 3 m, between approximately 2.5 m and 2.6 m, including values such as 2.5 m, 2.55 m, 2.6 m, and/or other suitable vales, both larger and smaller. The tapered section 210 of the proximal portion 172 can have a length 216. The length 216 can be any suitable length. For maximum transmittance of light through the tapered section 210 into the section 220, the taper can be gradual. For example, the shape of the tapered section 210, the angle of the taper, and/or the length 216 can be selected to provide a gradual taper. For example, the length 216 of the tapered section 210 of the proximal portion 172 can be any value that is equal to or greater than approximately one hundred times the difference between the diameter 214 and the diameter 224. For example, the diameter 224 can be 25 microns, and the diameter 214 can be 75 microns (e.g., the parameter N multiplied by the diameter 224, with N=3, or 3·25 μm). For maximum throughput, the length 216 can be any length longer than 5 mm (e.g., 100·(75 μm−25 μm)). The section 220 within the central portion 176, which has a constant shape, can have any suitable length 226. For example, the length 226 can between approximately 10 mm and approximately 1000 mm, between approximately 50 mm and approximately 500 mm, between approximately 100 mm and approximately 200 mm, including values such as 100 mm, 125 mm, 145 mm, 150 mm, 166 mm, 200 mm, and/or other suitable values both larger and smaller. The tapered section 230 of the distal portion 174 can have any suitable length 236. For example, the length 236 can between approximately 5 microns and approximately 1000 microns, between approximately 5 microns and 500 microns, between approximately 10 microns and 100 microns, including values such as 10 microns, 25 microns, 50 microns, 66 microns, 100 microns, and/or other suitable values both larger and smaller. The core/cladding diameter ratio can remain constant or change along the length 216 of the tapered section 210 and/or the length 236 of the tapered section 230.

Referring now to FIG. 2B, the condenser 126 can be configured to focus the condensed beam 127 at the beam spot 129. The beam spot 129 can be ideally centered within the port 129 and/or within the entrance aperture 212 of the optical fiber 170. As described herein, the entrance aperture 212 can be sized and shaped to accommodate angular or lateral misalignment of the beam spot 129 so as to preserve efficient optical coupling of the condensed beam 127 into the optical fiber 170. The beam spot 129 can be diffraction limited. The beam spot 129 can have a diameter 244. The value of the diameter 244 can be between approximately 1 μm and approximately 30 μm, between 1 μm and approximately 20 μm, 2 μm and approximately 15 μm, including values such as 2 µm, 8 µm, 12 µm, 15 µm, and/or other suitable values both larger and smaller.

The light beam originating from the light source 122 can be characterized by its angular spread or divergence at various locations within the optical path between the light source 122 and the surgical field 180 (FIG. 1). A metric of the angular spread can be the numerical aperture ("NA"). Formally, NA=sin(cone half angle). The light beam within the ophthalmic illumination system 100 can thus be characterized by the numerical aperture $NA_{beam}$. With reference to FIG. 2B, mathematical descriptions 270 (FIG. 2B), discussed in greater detail below, describe $NA_{beam}$ at various locations within the ophthalmic illumination system 100. The optical fiber 170 can also be characterized by an angular spread or numerical aperture $NA_{fiber}$ that describes the angles of light that can be accepted and transmitted by the optical fiber 170. The $NA_{fiber}$ can be a fixed characteristic for a given optical fiber 170. Different fibers can have different NAs. The optical fiber 170 can have any suitable numerical aperture $NA_{fiber}$, including an $NA_{fiber}$ between approximately 0.1 and approximately 0.9, between approximately 0.1 and approximately 0.8, between approximately 0.1 and approximately 0.7, including values such as 0.12, 0.22, 0.26, 0.30, 0.37, 0.44, 0.48, 0.50, 0.63, 0.66, and/or other suitable values both larger and smaller. The $NA_{fiber}$ can be selected such that the optical fiber 170 transmits light with the desired angular spread. When the light beam has a numerical aperture $NA_{beam}$ less than or equal to the numerical aperture $NA_{fiber}$, the light beam can be transmitted by the optical fiber 170 with little to no optical losses. With reference to FIG. 2B, when the light beam has a numerical aperture $NA_{beam}$ within the optical fiber 170 greater than the numerical aperture $NA_{fiber}$, a portion (e.g., the higher angle rays) of the light beam can be lost in the cladding 204. Another portion (e.g., the smaller angle rays) of the light beam that has a numerical aperture $NA_{beam}$ less than or equal to the numerical aperture $NA_{fiber}$ can transmitted by the optical fiber 170. In that regard, $NA_{beam}$ within the optical path between the light source 122 and the surgical field 180 can be related to the $NA_{fiber}$. The light beam at various points within the ophthalmic illumination system 100 can also be characterized by a beam diameter. Generally, within the optical fiber 170, the beam diameter of the light beam can be equal to the diameter of the optical fiber. The beam diameter and the numerical aperture $NA_{beam}$ can be chosen to fill the optical fiber 170 with light for efficient transmission to the surgical field 180.

A mathematical relationship can describe the angular spread and the beam diameter of the light transmitted by the optical fiber 170. For example, the product of the angular spread, such as the $NA_{beam}$, and the beam diameter can be constant. That is, the angular spread and the beam diameter can have a reciprocal relationship. Thus, as the beam diameter decreases, the angular spread increases and vice versa. For example, within the tapered region 210, as the beam diameter decreases (because the diameter of the core 202 decreases), the angular spread of the light can correspondingly increase. Similarly, within the tapered region 230, the angular spread of the light can increase as the beam diameter and the diameter of the core 202 decreases.

The mathematical descriptions 270 of the angular spread or the $NA_{beam}$ at various points 254, 256, and 258 within the ophthalmic illumination system 100 can be illustrated in FIG. 2B. The condenser 126 can be configured to direct the condensed beam 127 to the optical fiber 170 such that that the $NA_{beam}$ within the optical fiber 127 does not exceed the $NA_{fiber}$. In that regard, the $NA_{beam}$ of the condensed beam 127 can be based on the diameter 214 of the entrance aperture 212. For example, the $NA_{beam}$ of the condensed beam 127 can be based on the parameter N. As described above, the diameter 214 of the entrance aperture 212 can also be related to the parameter N. The condenser 126 can be configured to focus the condensed beam 127 such that that the condensed beam 127 has an angular spread based on the diameter 214 of the entrance aperture 212. The point 254 can be located at the beam spot 129, where the condensed beam 127 interfaces with the entrance aperture 212. As shown by the mathematical relationship 270 at point 254, the condenser 126 configured to focus the condensed beam 127 such that that $$NA_{beam} = \frac{NA_{fiber}}{N}.$$

The condensed beam 127 can be coupled into the optical fiber 170 at the entrance aperture 212 having a diameter $N \cdot d_{fiber}$. The $NA_{beam}$ increases by a factor of the parameter N within the tapered region 210 as the diameter of the 202 decreases by a factor of the parameter N.

The condenser 126 focusing the condensed beam 127 with $$NA_{beam} = \frac{NA_{fiber}}{N}$$

can thus account for the increase in angular spread or $NA_{beam}$ within the tapered region 210. Accordingly, as shown by the mathematical relationship 270 at point 256, within the central portion 176 of the optical fiber 170, the light beam has $NA_{beam}=NA_{fiber}$. As discussed above, efficient optical transmission occurs within the optical fiber 170 when $NA_{beam}=NA_{fiber}$. The $NA_{beam}$ increases within the tapered region 230 as the diameter of core 202 within the distal portion 176 decreases. The tip 232 can also be sized and shaped to scatter or increase the angular spread of the light beam. As shown by the mathematical relationship 270 at point 258, the optical fiber 170 can be configured to deliver the emitted light 162 with $NA_{beam} \gg NA_{fiber}$.

The condenser 126 can have an effective focal length 246. The effective focal length 246 can be a description of the distance the condensed beam 127 travels between the condenser 126 and the beam spot 129. Fold mirror(s), beam splitters, and/or other optical components can be disposed in the optical path between the light source 122 and the optical fiber 170, including between the condenser 126 and the optical fiber 170. The value of the effective focal length 246 can be between approximately 5 mm or smaller and 150 mm or greater, including values between 8 mm and 50 mm. The condenser 126 can be positioned such that it has the effective focal length 246 based on the diameter 214 of the entrance aperture 212 of the proximal portion 172 of the optical fiber 170.

Figure 3:
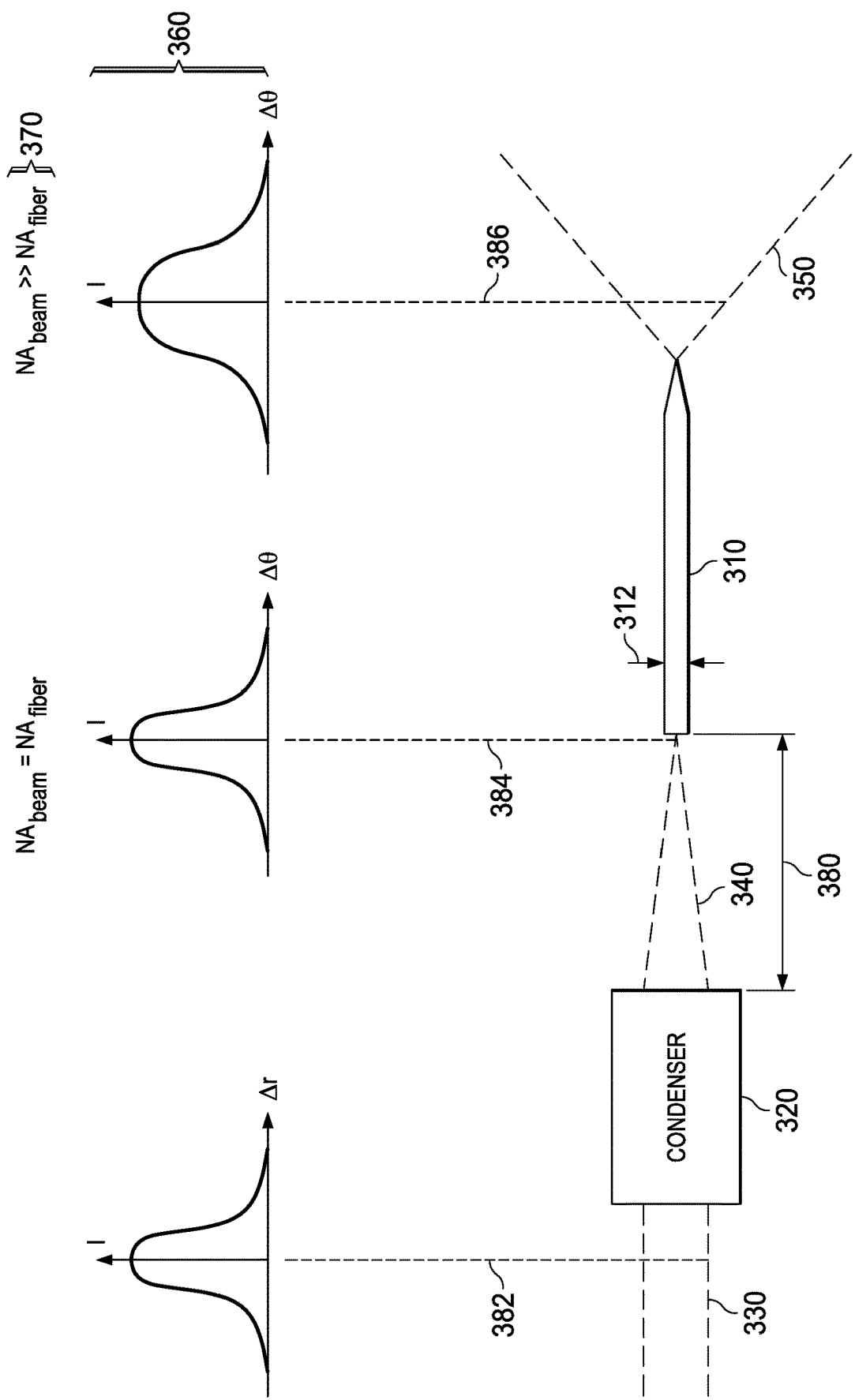
FIG. 3 is a diagram illustrating an arrangement of a condenser and an optical fiber.

FIG. 3 illustrates an arrangement including an optical fiber 310 and a condenser 320. In contrast to optical fiber 170 of FIGS. 1, 2A, and 2B, the optical fiber 310 of FIG. 3 does not include a tapered proximal section. Rather, the proximal and central portions of the optical fiber 310 have a constant diameter 312. Collimated beam 330 can be focused by the condenser 320. A point 384 identifies a location within the arrangement of FIG. 3 where a condensed beam 340 encounters the optical fiber 310. As shown by mathematical relationship 370 at point 384, the condensed beam 340 can have $NA_{beam}=NA_{fiber}$. The $NA_{beam}$ when the condensed beam interfaces with the optical fiber can be smaller, by a factor of the parameter N in FIG. 2B (point 254), compared to FIG. 3 (point 384). The light within the optical fiber 310 of FIG. 3 also has $NA_{beam}=NA_{fiber}$. The mathematical relationship 370 at point 386 illustrates that emitted light 350 can have $NA_{beam}>>NA_{fiber}$. The condenser 320 has an effective focal length 380.

Referring again to FIG. 2B, the effective focal length 246 of the condenser 126 can be relatively longer than the effective focal length 380 (FIG. 3), for equal diameters of the collimated beam 125 (FIG. 2B) and the collimated beam 330 (FIG. 3). For example, the effective focal length 246 can be greater than the effective focal length 380 by a factor of the parameter N. In that regard, the effective focal length 246 can be based on the parameter N also associated with the diameter 129 of the entrance aperture 212. The relatively longer effective focal length 246 can allow the $NA_{beam}$ to be reduced by a factor of the parameter N, at the point 254. The condensed beam 127 can be coupled into the optical fiber 170 at the point 254. The effective focal length 246 of the condenser 126 can be configured to have a relatively larger effective focal length 246 because the optical fiber 170 includes the tapered section 210.

With reference to FIG. 2B, the shape of the light beam at points 252, 254, 256, and 258 can be illustrated in graphs 260. In that regard, the graphs 260 include cross-sectional profile of the irradiance of light beam on the y-axis and the radial position from the center of the light beam on the x-axis. The illustrated light beam can be generally Gaussian at all points 252, 254, 256, and 258. The light beam may be configured to have any suitable beam shape, such as through use of a beam shaper positioned any point within optical path between the light source 122 and the surgical field 180. For example, the light beam may have a flat top beam profile or other desired shape. The relatively narrow, small diameter beam spot 129 can be illustrated by the relatively narrow Gaussian profile of the graph 260 at the point 254. Graphs 360 of FIG. 3 similarly illustrate the shape of the light beam at points 382, 384, 386 in the arrangement of the condenser 320 and the optical fiber 310. Compared to the relatively narrow, small diameter beam spot 129 (FIG. 2B), the Gaussian profile of the graph 360 at the point 254 can be relatively wider, indicating a relatively larger diameter beam spot.

Referring again to FIGS. 2A and 2B, the present disclosure can improve performance of the ophthalmic illumination system 100, such as decreasing the sensitivity of the optical fiber 170 to misalignment of the light source 122, the collimator 124, the condenser 126, and/or the optical fiber 170 that occurs after assembly of the ophthalmic illumination system 100. The factors influencing angular sensitivity can include: (1) the diameter of the collimated light beam 125 into the condenser 126; (2) a toleranced core diameter of the optical fiber 170; and (3) the mathematical relationship $NA_{beam}=NA_{fiber}$ for efficient propagation of light through the optical fiber 170. These three factors can sometimes be difficult to change, which causes optical misalignment sensitivity to remain high. For example, the diameter of the collimated beam 330 can be fixed by the design of a light source and a collimator in some instances.

Referring to FIGS. 2A and 2B, the present disclosure describes increasing diameter of the core 202 (e.g., within the tapered section 210) and decreasing the $NA_{beam}$ of the condensed beam 127 by a factor of the parameter N. Such changes can have a positive impact on the ophthalmic illumination system 100 by decreasing sensitivity to optical misalignment. Thus, advantageously, the coupling efficiency can be less likely to be decreased and/or decreases by a smaller amount as a result of angular or lateral misalignment. An angular sensitivity parameter $\theta_N$ can be characterized as the maximum off-axis angle of the collimated beam 125 into the condenser 126 before significant fiber coupling efficiency losses start to occur. A higher $\theta_N$ corresponds to a more forgiving system for optical misalignment because the higher off-axis angles can be efficiently coupled into the optical fiber 170. Generally, the description herein uses some specific example quantities so that some calculations can be more easily understood. The specific quantities can be exemplary only. Any suitable value can be used in different examples.

Figure 4:
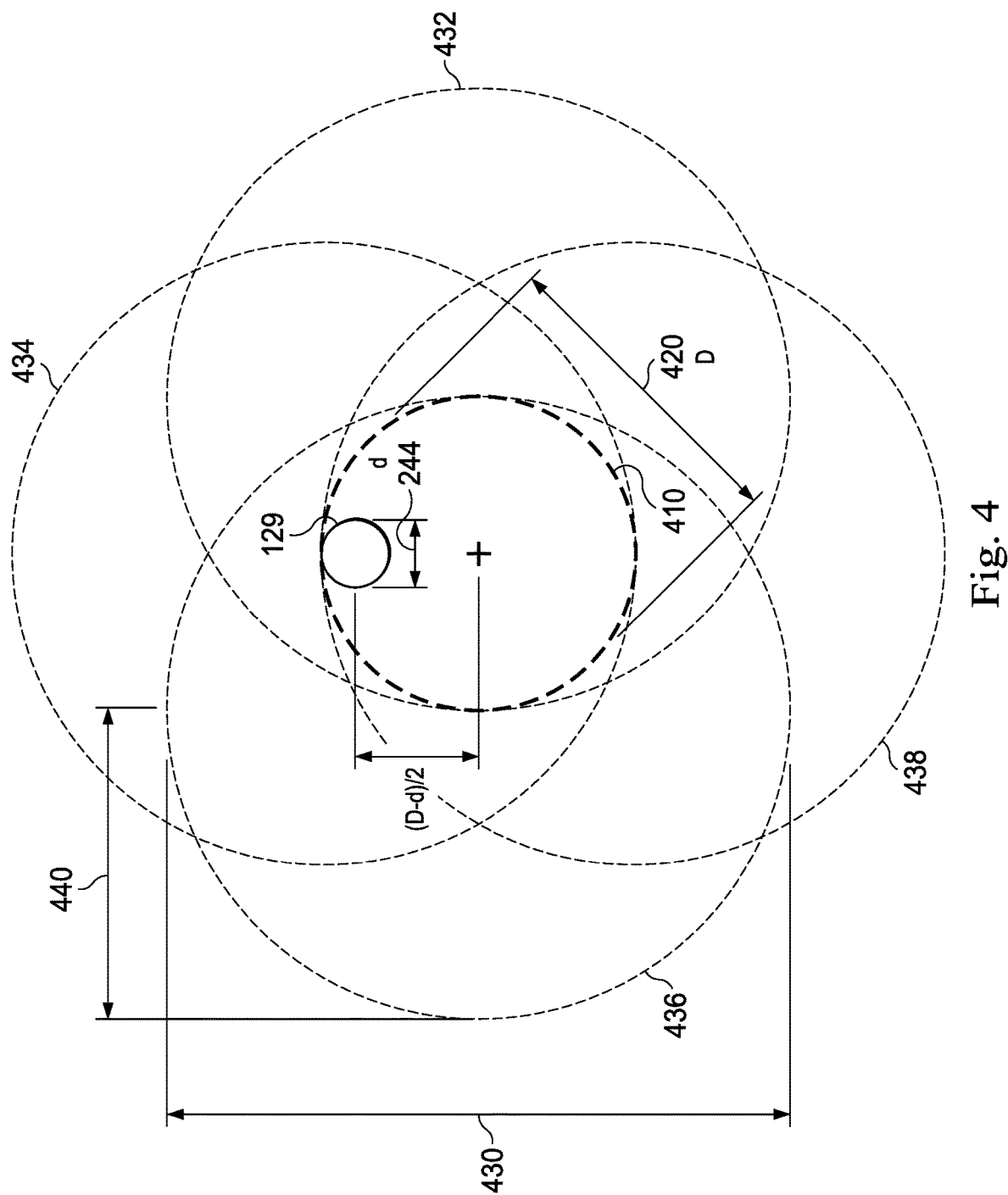
FIG. 4 is a diagram illustrating en face views of a beam spot, different positions of an optical fiber core when coupled to a housing, and a toleranced core diameter that is aligned in different positions of the optical fiber core.

As an approximation, $\theta_N$ can be given by:

$$\theta_N = \frac{D_N - d_N}{2f_N},$$

where $D_N$ indicates the toleranced core diameter for N, $d_N$ indicates the diameter 244 of the beam spot 129 of the condensed beam 127, and $f_N$ indicates the effective focal length 246 for N. Some of these variables can be graphically illustrated in FIG. 4. In that regard, FIG. 4 can illustrate en face views of the beam spot 129, a toleranced core 410, and different positions 432, 434, 436, and 438 of an entrance aperture of an optical fiber. The beam spot 129 can have the diameter 244. The different positions 432, 434, 436, and 438 can represent alignment of the proximal face or entrance aperture of the optical fiber relative to a housing or a condensed beam. The different positions 432, 434, 436, and 438 can result from manufacturing tolerances of the optical fiber, the housing, and/or the port facilitating coupling between the optical fiber and the housing. Repetition of exact positioning of the optical fiber difficult can be difficult given the manufacturing tolerances of the optical fiber, the housing, and/or the port. As shown, some portions of the entrance aperture at the different positions 432, 434, 436, and 438 can overlap while others do not. A diameter 420 of the toleranced core 410 can represent consistent alignment of a portion of the entrance aperture, relative to a condensed beam, at each of the positions 432, 434, 436, 438. In that regard, the entrance aperture at each of the positions 432, 434, 436, and 438 can have a diameter 430. Each of the positions 432, 434, 436, and 438 can also have an uncertainty or error associated with it, indicated by the length 440. Generally, the diameter 420 of the toleranced core 410 can be the difference of the diameter 430 of the entrance apertures and the length 440 representing the position uncertainty of the optical fibers. Despite the relatively larger diameter 430 of the entrance aperture, the diameter 420 of the toleranced core 410 can be relatively small. For example, the diameter 420 of toleranced core 410 can be 7 μm for an optical fiber with an actual core diameter of 25 μm.

As an approximation, the effective focal length $f_N$ for general N can be related to the effective focal length $f_1$ for N=1 by $f_N=N \cdot f_1$. In that regard, N=1 can correspond to the arrangement of FIG. 3, in which the optical fiber does not include a tapered proximal portion.

As an approximation, the beam spot diameter $d_N$ for general N can be related to the beam spot size $d_1$ for N=1 by $d_N=N \cdot d_1$. In that regard, the diffraction-limited (and in general, the non-diffraction limited) beam spot diameter can be proportional to effective focal length $f_N$ of the condenser and therefore proportional to the parameter N. As the effective focal length $f_N$ increases with increasing N, the beam spot diameter $d_N$ also increases. For an optically well-designed condenser with N=1, the diameter of the beam spot can be, at worst, only slightly larger than the diffraction-limited spot size.

As described herein, an example of a toleranced core diameter $D_N$, in microns or μm, can be $D_N$=25N—18. The example term "25N" represents the actual core diameter of the entrance aperture of the optical fiber, represented by diameter 430 in FIG. 4. The example 18 μm corresponds to the uncertainty in the position and/or alignment of the optical fiber core, represented by length 440 in FIG. 4. The optical fiber 170 can have any suitable core diameter, with 25 μm being an example. As indicated by the mathematical description of $D_N$, the actual core diameter of the entrance aperture increases by a factor of N while the positional uncertainty remains constant. Thus, the toleranced core diameter, which represents the portion of the optical fiber core consistently positioned to receive the condensed beam, increases significantly with N. For example, when N=1, $D_N$=7 μm, and when N=3, $D_N$=57 μm. As shown with this example, the toleranced core diameter $D_N$ increases by a factor of approximately eight while the parameter N increases by a factor of three. This rapid increase in the toleranced core diameter $D_N$ with the parameter N facilitates greater tolerance of optical misalignment in the ophthalmic illumination system 100. In that regard, the toleranced core diameter $D_N$ increases with increasing N faster than the beam spot diameter $d_N$ and the effective focal length $f_N$ increase. As shown in the calculation below, because toleranced core diameter $D_N$ increases faster than the beam spot diameter $d_N$ and the effective focal length $f_N$, the angular sensitivity parameter $\theta_N$ or the maximum off-axis angle that maintains efficient coupling also increases.

Substituting the values for $f_N$, $d_N$, and $D_N$ into the formula for $\theta_N$ yields:

$$\theta_N = \frac{(25N - 18) - (Nd_1)}{2(Nf_1)}.$$

For N=1, which indicates an arrangement similar to that illustrated in 3, $$\theta_1 = \frac{7 - d_1}{2f_1}.$$

$\theta_1$ can be calculated by identifying the values of $d_1$ and $f_1$. The root mean square (RMS) beam spot diameter of the condensed beam 340 from the condenser 320 or $d_1$ can be 2.58 μm, for example. The effective focal length 380 or $f_1$ can be calculated based on an arrangement of the condenser 320 shown in FIG. 5. In that regard, the effective focal length 380 can be described by $$f_1 = \frac{a}{\tan\beta}.$$

A radius α can describe the radius of the collimated beam 330. For example, the radius α can equal 2.65 mm. The angle β can be the marginal ray angle at the $1.3 \times 1/e^2$ point. The angle β can be 17.9°, for example. Inserting these values for the radius α and the angle β into the equation above, $f_1$ or the effective focal length 380 can be calculated to be 8.20 mm or 8200 μm. The arrangement of FIG. 5 includes a beam splitter 530, which directs the condensed beam 340 as necessary given the physical constraints of a housing.

Inserting the example values for $d_1$ and $f_1$ into the equation above for $$\theta_1 = \frac{7 - 2.58}{2(8200)} = 0.270 \text{ mrad} = 0.015°.$$

Referring to FIG. 3, $\theta_1$=0.015° can describe the maximum off-axis angle of the collimated beam 330 into the condenser 320 before significant fiber coupling efficiency losses start to occur. The optical fiber 310 can have a toleranced core diameter of 7 μm for an actual core diameter 312 of 25 μm. The illumination optics illustrated in FIG. 3 can have ≥72% transmittance (manufacturing tolerances included), including diffraction encircled energy through the 7 μm toleranced core diameter and transmittance through the angular numerical aperture of the optical fiber 310. A maximum allowable off-axis angular error of a collimated beam 330 into a condenser 320 of 0.0134° results in a drop in diffraction-encircled energy through the 7 μm toleranced core diameter to 90% at 650 nm. The computed $\theta_1$=0.015° can be approximately equal to the 0.0134° theoretical value calculated by optical ray tracing using a software application, such as Zemax.

A figure of merit $$r_N = \frac{\theta_N}{\theta_1}$$

can gauge the how effective of the ophthalmic system 100 of FIGS. 1, 2A, 2B, with N>1, accommodates optical misalignment while maintaining high coupling efficiency. The figure of merit $r_N$ compares the maximum off-axis angle that maintains optical coupling for N>1 to the maximum off-axis angle of N=1. More specifically, $$r_N = \frac{\theta_N}{\theta_1} = \frac{\frac{(25N - 18) - (Nd_1)}{2(Nf_1)}}{\frac{7 - d_1}{2f_1}} = \frac{25 - d_1}{7 - d_1} - \frac{18}{N(7 - d_1)}.$$

The first term of $r_N$ can be constant with N and dependent only on $d_1$. The second term can be N-dependent and decrease with increasing N for $d_1$<7 μm. In the limit of N=∞, $r_N$ asymptotically approaches the first term.

Figures 5, 6:
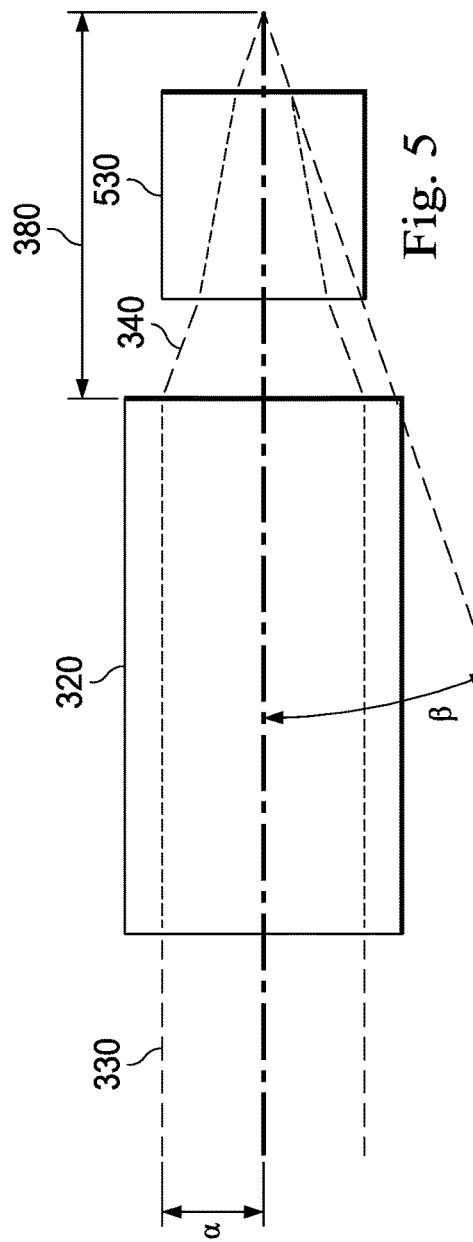
FIG. 5 is a diagram illustrating an arrangement of a condenser.
FIG. 6 is a chart illustrating a figure of merit $r_N$ comparing how much more optical misalignment can be tolerated, while maintaining high coupling efficiency, by an optical fiber including a tapered proximal portion relative to an optical fiber with similarly-sized proximal and central portions.

Values of $r_N$ for varying N and $d_1$ can be tabulated in chart 600 of FIG. 6. The values of chart 600 indicate an advantageous decrease in the post-alignment angular sensitivity of the ophthalmic illumination system 100. In that regard, $r_N$ can describe a multiple by which the maximum off-axis angle that maintains efficient optical coupling increases, with N>1, relative to the arrangement of FIG. 3, with N=1. For example, given a RMS beam spot diameter $d_1$ equal to 2.58 μm then, assuming $d_1$ equals 3 μm, $r_N$=3.25 for N=2. That is, the maximum off-axis angle that maintains efficient optical coupling can be increased by a factor of 3.25 when N=2. Such a system can be more tolerant of optical misalignment because of efficient coupling of higher off-axis angles of light into the optical fiber. The figure of merit $r_N$ increases to 5.5 at the limit N=∞.

FIG. 7 includes a graph 700 that plots values of $r_N$ for varying N for different $d_1$. The x-axis can include values of the parameter N. The y-axis can include values of the figure of merit $r_N$. The curves 710, 720, and 730 correspond to $d_1$ equal to 1 µm, 2 µm, and 3 µm. Simulated results 740 of actual condenser/fiber systems with parameter N values of 2, 3, 4 and 5 and with a focused beam spot size $d_1$ of approximately 1.95 µm can also be included in the graph 700. The correspondence between the simulated results 740 and the curve 720 can be an indication of the validity of the mathematical relationship $r_N$.

The calculations of figure of merit $r_N$ and/or the angular sensitivity parameter $\theta_N$ can be used by a manufacturer to determine one or more quantities associated the ophthalmic illumination system 110. For example, the calculations can be part of an algorithm used to select the parameter N. The parameter N can be used to determine the diameter 214 of the entrance aperture 212, the effective focal length 246 of the condenser 126, the angular spread or $NA_{beam}$ of the condensed beam 127, and/or other suitable quantities. The optical fiber 170 can be manufactured or selected based on the chosen diameter 214. The condenser 126 can be positioned within the housing 121 relative to the light source 122, the collimator 124, and/or the optical fiber 170, based on the chosen effective focal length 246 and/or $NA_{beam}$.

Embodiments as described herein can provide devices, systems, and methods that facilitate greater tolerance for misalignment of the light beam and preservation of high coupling efficiency into the optical fiber despite the alignment errors. The examples provided above can be exemplary in nature and not limiting. One skilled in the art may readily devise other systems consistent with the disclosed embodiments intended to be within the scope of this disclosure. As such, the application can be limited only by the following claims.

The invention claimed is:

1. An apparatus, comprising:
an optical fiber having a core diameter and configured to transmit a light beam output by a light source and focused by a condenser, the optical fiber including:
a proximal portion configured to receive the light beam focused by the condenser onto a focal point at the proximal portion, the proximal portion comprising a first tapered portion comprising a proximal end having a core diameter $D_1$ and a terminal end having a core diameter $D_2$, wherein $D_1$ is greater than $D_2$,
a distal portion configured to emit the light beam to illuminate a surgical field, and
a central portion extending between the proximal portion and the distal portion, wherein the core diameter is constant over the central portion;
wherein at the focal point on the proximal portion of the optical fiber, a numerical aperture of the light beam ($NA_{beam}$) equals (a numerical aperture of the optical fiber ($NA_{fiber}$)) divided by N, wherein N equals the core diameter $D_1$ divided by a core diameter of the central portion;
wherein the central portion is configured such that the numerical aperture of the light beam $NA_{beam}$ is equal to a numerical aperture of the central portion $NA_{fiber}$.

2. The apparatus of claim 1, wherein the proximal portion of the optical fiber includes a straight section positioned proximal to the first tapered portion.

3. The apparatus of claim 1, wherein a core diameter of the proximal portion of the optical fiber is a multiple of the core diameter of the central portion of the optical fiber.

4. The apparatus of claim 3, wherein the condenser is configured to have an effective focal length based on the core diameter of the proximal portion of the optical fiber.

5. The apparatus of claim 4, wherein the condenser is configured to focus the light beam such that an angular spread of the light beam focused by the condenser is based on the core diameter of the proximal portion of the optical fiber.

6. The apparatus of claim 4, wherein the condenser is configured to focus the light beam such that an angular spread of the light beam focused by the condenser is less than an angular spread of the light beam transmitted by the optical fiber.

7. The apparatus of claim 4, wherein the condenser is configured to focus the light beam such that an angular spread of the light beam focused by the condenser is a fractional multiple of an angular spread of the light beam transmitted by the optical fiber.

8. The apparatus of claim 1, wherein a diameter of the light beam is equal to a toleranced core diameter of the optical fiber minus (a maximum off axis angle of collimated beam into the condenser) times 2 times an effective focal length for N.

9. The apparatus of claim 1, further comprising:
the light source;
the condenser; and
a surgical instrument configured to be positioned within the surgical field and coupled to the optical fiber.

10. A method, the method comprising:
focusing, using a condenser, a light beam emitted by a light source onto a focal point at a proximal portion of an optical fiber, the optical fiber including the proximal portion, a distal portion, and a central portion extending between the proximal portion and the distal portion, wherein the proximal portion comprises a first tapered portion comprising a proximal end having a core diameter $D_1$ and a terminal end having a core diameter $D_2$, wherein $D_1$ is greater than $D_2$; and wherein the core diameter is constant over the central portion, wherein at the focal point on the proximal portion of the optical fiber, a numerical aperture of the light beam ($NA_{beam}$) equals (a numerical aperture of the optical fiber ($NA_{fiber}$)) divided by N, wherein N equals the core diameter $D_1$ divided by a core diameter of the central portion; and
transmitting, using the optical fiber, the light beam to a surgical field;
wherein the central portion is configured such that the numerical aperture of the light beam $NA_{beam}$ is equal to a numerical aperture of the central portion $NA_{fiber}$.

11. The method of claim 10, wherein focusing the light beam includes focusing the light beam onto a straight section or a tapered section of the proximal portion of the optical fiber.

12. The method of claim 10, wherein focusing the light beam includes focusing the light beam using the condenser having an effective focal length based on a core diameter of the proximal portion of the optical fiber.

13. The method of claim 10, wherein focusing the light beam includes focusing the light beam using the condenser such that an angular spread of the light beam is based on a core diameter of the proximal portion of the optical fiber.

14. An apparatus, comprising:
an optical fiber having a core diameter and configured to transmit a light beam output by a light source and focused by a condenser, the optical fiber including:
  a proximal portion configured to receive the light beam focused by the condenser onto a focal point at the proximal portion, the proximal portion comprising a first tapered portion in which the core diameter varies distally;
  a distal portion configured to emit the light beam to illuminate a surgical field, and
  a central portion extending between the proximal portion and the distal portion, wherein the core diameter is constant over the central portion;
  wherein at the focal point on the proximal portion of the optical fiber, a numerical aperture of the light beam ($NA_{beam}$) equals (a numerical aperture of the optical fiber ($NA_{fiber}$)) divided by N, wherein N equals a core diameter $D_1$ divided by a core diameter of the central portion; and
  wherein the central portion is configured such that a numerical aperture of the light beam $NA_{beam}$ is equal to a numerical aperture of the central portion $NA_{fiber}$.

15. The apparatus of claim 14, wherein:
the proximal portion comprises a first section proximal to the first tapered portion; and
the core diameter of the fiber is constant over the first section of the proximal portion.

16. The apparatus of claim 14, wherein the distal portion comprises a second tapered portion over which the core diameter of the optical fiber varies distally.

17. The apparatus of claim 14, wherein:
the core diameter of the first tapered portion decreases distally; and
the distal portion comprises a second tapered portion over which the core diameter of the optical fiber decreases distally.

18. The apparatus of claim 14, wherein the condenser is configured to focus the light beam such that an angular spread of the light beam focused by the condenser is less than an angular spread of the light beam transmitted by the optical fiber.

19. The apparatus of claim 14, wherein the condenser is configured to focus the light beam such that an angular spread of the light beam focused by the condenser is a fractional multiple of an angular spread of the light beam transmitted by the optical fiber.

20. The apparatus of claim 14, wherein a diameter of the light beam is equal to a tolloranced core diameter of the optical fiber minus (a maximum off axis angle of collimated beam into the condenser) times 2 times an effective focal length for N.

* * * * *